(12) United States Patent
Georgakoudi et al.

(10) Patent No.: US 12,035,893 B2
(45) Date of Patent: Jul. 16, 2024

(54) LAPAROSCOPIC IMAGING USING POLARIZED LIGHT

(71) Applicants: Trustees of Tufts College, Boston, MA (US); Lahey Clinic, Inc., Burlington, MA (US)

(72) Inventors: Irene Georgakoudi, Acton, MA (US); Martin Hunter, Bradford, MA (US); Robert Michael Trout, Medford, MA (US); Thomas Schnelldorfer, Arlington, MA (US)

(73) Assignees: Trustees of Tufts College, Boston, MA (US); Lahey Clinic, Inc., Burlington, MA (US)

( * ) Notice: Subject to any disclaimer, the term of this patent is extended or adjusted under 35 U.S.C. 154(b) by 563 days.

(21) Appl. No.: 17/284,413

(22) PCT Filed: Oct. 11, 2019

(86) PCT No.: PCT/US2019/055896
§ 371 (c)(1),
(2) Date: Apr. 9, 2021

(87) PCT Pub. No.: WO2020/077237
PCT Pub. Date: Apr. 16, 2020

(65) Prior Publication Data
US 2021/0345867 A1 Nov. 11, 2021

Related U.S. Application Data

(60) Provisional application No. 62/744,991, filed on Oct. 12, 2018.

(51) Int. Cl.
*G01J 3/02* (2006.01)
*A61B 1/00* (2006.01)
(Continued)

(52) U.S. Cl.
CPC ........ *A61B 1/0646* (2013.01); *A61B 1/00096* (2013.01); *A61B 1/00128* (2013.01);
(Continued)

(58) Field of Classification Search
CPC .............. A61B 1/0646; A61B 1/00096; A61B 1/00128; A61B 1/00137; A61B 1/042;
(Continued)

(56) References Cited

U.S. PATENT DOCUMENTS 7,289,211 B1 * 10/2007 Walsh, Jr. ................. G01J 4/04
356/369
8,125,648 B2 * 2/2012 Milner ............... G01B 9/02091
356/497

(Continued)

FOREIGN PATENT DOCUMENTS

WO 2020077237 A1 4/2020

OTHER PUBLICATIONS

International Search Report and Written Opinion, PCT/US2019/055896, dated Dec. 23, 2019, 10 pages.
(Continued)

*Primary Examiner* — Abdullahi Nur
(74) *Attorney, Agent, or Firm* — Potomac Law Group, PLLC; Reza Mollaaghababa; Amanda Y. Baker (57) ABSTRACT

Methods and apparatus for improved imaging of internal tissue structures, such as lesions in the peritoneum, are disclosed employing Differentially Polarized Light (DPL) imaging. The optical system can include a laparoscope having at least one optical illumination waveguide for directing illuminating radiation and an optical collection waveguide having an aperture for collecting and transmitting radiation backscattered from a tissue region to a detector. The system further can include a polarizer for polarizing the illuminating radiation and a second analyzing polarizer
(Continued)

disposed in the optical return path, whereby backscattered radiation of differing polarizations can be passed to the detector. End cap assemblies are also disclosed that that can be fitted to conventional laparoscopes, e.g., by a threaded connection or the like, to facilitate DPL imaging by polarizing the illuminating light of the laparoscope. For example, the end cap can include a polarizing film within a stainless steel housing. The polarizing film can be shaped to cover of the illumination outputs of the laparoscope, while leaving clear the aperture for collection of reflected or scattered radiation.

18 Claims, 11 Drawing Sheets

(51) Int. Cl.
    *A61B 1/04*    (2006.01)
    *A61B 1/06*    (2006.01)
    *A61B 1/07*    (2006.01)
    A61B 1/313   (2006.01)

(52) U.S. Cl.
    CPC .......... *A61B 1/00137* (2013.01); *A61B 1/042* (2013.01); *A61B 1/0638* (2013.01); *A61B 1/0669* (2013.01); *A61B 1/07* (2013.01); *A61B 1/3132* (2013.01)

(58) Field of Classification Search
    CPC ....... A61B 1/0638; A61B 1/0669; A61B 1/07; A61B 1/3132; A61B 1/00186; G01J 3/28; G01J 3/02
    See application file for complete search history.

(56) References Cited

U.S. PATENT DOCUMENTS

| | | |
|---|---|---|
| 8,764,633 B2 | 7/2014 | McDowall |
| 2003/0043476 A1 | 3/2003 | Snively et al. |
| 2007/0185384 A1* | 8/2007 | Bayer ................ A61B 1/00177 600/129 |
| 2008/0062429 A1 | 3/2008 | Liang et al. |
| 2008/0249371 A1 | 10/2008 | Beckman et al. |
| 2009/0009759 A1* | 1/2009 | Backman .............. G01J 3/0208 356/303 |
| 2011/0152625 A1 | 6/2011 | Smith |
| 2013/0107274 A1 | 5/2013 | Vertikov et al. |
| 2015/0018645 A1* | 1/2015 | Farkas ................ A61B 5/0077 600/317 |
| 2018/0284417 A1 | 10/2018 | Deisseroth et al. |

OTHER PUBLICATIONS

International Preliminary Report on Patentability, PCT/US2019/055896, dated Apr. 22, 2021, 10 Pages.

\* cited by examiner

LAPAROSCOPIC IMAGING USING POLARIZED LIGHT

REFERENCE TO RELATED APPLICATIONS

This application is a 35 U.S.C. 371 national stage filing of International Application No. PCT/US2019/055896, filed on Oct. 11, 2019, which claims priority from U.S. Patent Provisional Application No. 62/744,991, filed Oct. 12, 2018, the contents of which including all appendices are herein incorporated by reference in their entireties.

GOVERNMENT SUPPORT

This invention was made with government support under grant number EB023498 awarded by the National Institutes of Health. The government has certain rights in the invention.

BACKGROUND

The present invention relates generally to operative and non-invasive imaging, such as laparoscopy, thoracoscopy, and endoscopy, for detecting occult tissue abnormalities, such as neoplasms, cancer metastases, fibrosis, wound healing, and endometriosis.

For cancer patients, prognosis and treatment selection fundamentally rely on the staging assessment of the underlying cancer, e.g., determining the absence or presence of distant metastases. Despite improvements in the available staging tools, including cross-sectional radiographic imaging and laparoscopy, the accuracy of staging for gastrointestinal and gynecologic malignancies varies tremendously, with "under-staging" considered as a common problem. Up to 30% of patients with these malignancies have distant recurrence of cancer after major resections with curative intent.

In the United States alone, this "understaging" problem is estimated to be about 15,000 patients per year. Metastatic recurrences of cancer, which often occur on the surface of the peritoneum, are thought to arise from the inability of conventional methods to detect small metastases (typically less than 3 mm in size) during initial staging. Although promising new immunotherapies for metastatic cancers are in development, the inability to detect early stage metastases can delay or compromise further treatment options.

The current intraoperative standard applied to screen for peritoneal metastases is the deployment of a laparoscope that pierces the abdominal wall to permit visual inspection of the peritoneum. Unfortunately, utilizing current laparoscopic imaging techniques, the sensitivity with which a clinician can identify the presence of these lesions is unsatisfactory, with false negative rates reportedly as high as 36 percent. The tendency of illuminating light to penetrate into the tissue beyond clinically relevant depths before returning to the collection aperture of the laparoscope results in images that often lack sufficient clarity to identify tissue abnormalities localized to the tissue surface, including metastatic lesions.

Differentially polarized light (DPL) imaging has been proposed for various biomedical applications as a way of improving surface image contrast. Generally speaking, DPL imaging allows one to distinguish light that has been singly-scattered from a tissue surface from light that has undergone numerous scattering events deeper in tissue, thereby providing an enhanced surface image.

However, despite this potential advantage in surface imaging, DPL techniques have not been generally adopted for laparoscopy. It has proven difficult to incorporate the necessary polarizing structures into conventional laparoscopes. Accordingly, there exists a need for better laparoscopic imaging systems and better methods for detecting tissue abnormalities.

SUMMARY OF THE INVENTION

Methods and apparatus for improved imaging of internal tissue structures, such metastatic cancer lesions in the peritoneum, are disclosed employing differentially polarized light (DPL) imaging. In comparison to conventional imaging, it has been found that substantially increased contrast of tissue surface features can be achieved with DPL imaging, particularly color DPL imaging. Methods are also disclosed for enhancing DPL imaging utilizing white light or distinct wavelength bands for illumination and color charge coupled devices (color CCDs) for detection.

In one aspect of the invention, optical systems are disclosed including a laparoscope having an optical input port for receiving illuminating radiation, at least one optical illumination waveguide (e.g., fiber optic or lens rod) for directing illuminating radiation from the input port to a distal end of the waveguide, and an optical collection waveguide having a distal end aperture for collecting backscattered radiation from the tissue region and further having a proximal end for transmitting the backscattered radiation to a detector, the detector and optical collection waveguide defining an optical return path. The system further can include a polarizer positioned at the distal end of the illumination waveguide configured to polarize the illuminating radiation and direct polarized illuminating radiation onto a target tissue region to be examined, at least one lens disposed in the optical return path for imaging the tissue region unto the detector, and a second analyzing polarizer also disposed in the optical return path, whereby backscattered radiation of distinct polarizations can be passed to the detector. In certain embodiments, the lens can advantageously be an adjustable focus or zoom lens. Moreover, the system can further include a variable wavelength retarder also disposed in the optical return path to facilitate serial acquisition of two or more images of differing polarization. Alternatively, in another embodiment a CCD camera can be incorporated into distal end optics along with appropriate analyzer filters.

In another aspect of the invention, a polarizing end cap is disclosed for placement on conventional laparoscopes to permit their use in DPL systems. The optical accessory can be an end cap having a polarizing film that covers one or more illumination outputs of the laparoscope, while leaving a collection aperture clear. The optical accessory can take the form of a removable sleeve with optical filters at the distal end of the laparoscope, to linearly polarize the white light used to illuminate the target tissue region. At the proximal end, a liquid crystal variable wavelength retarder can be employed in conjunction with a linear polarizer for automated, near video-rate collection of images that differ in polarization, e.g., images polarized in either parallel (co-polarized) or perpendicular (cross-polarized) geometries relative to the polarized light incident on the peritoneum. Alternatively, differing circular rather than linear polarizations can be employed in the return path in conjunction with circularly polarized illumination to acquire similar differential images.

In yet another aspect of the invention, methods are disclosed for significantly improving the staging accuracy of peritoneal laparoscopy by increasing its capacity to detect such small, occult metastases. Polarization-gating is employed to highlight surface features, and thereby increase the detection sensitivity for superficial peritoneal metastases. In one embodiment, polarized radiation can be used to illuminate the target tissue region. Scattered radiation co- and cross-polarized to the illumination can be detected. A differential signal corresponding to a difference between the intensities of the detected scattered radiation at those two polarizations can be analyzed to derive information about tissue structure and/or detect abnormalities. This analysis can be performed at two or more different wavelengths (or wavelength bands) or with white light illumination and color images obtained via a multi-pixel color detector. As will be explained further below, the optical retarder can be set to obtain a desired or optimal image quality for a particular color or wavelength band without unduly compromising other wavelengths.

DETAILED DESCRIPTION

When target tissue is illuminated with linearly polarized light, reflected light is received from both the surface and the bulk of the tissue. Reflectance originating from deeper within the sample follows a longer optical path and becomes randomly polarized. In contrast, the surface reflectance from biological tissues predominantly retains the direction of the incident polarization, and is mostly co-polarized to the illumination.

The distinction between the polarization states of the surface and bulk signals is exploited in differentially polarized light imaging in order to remove the bulk signal, leaving the surface signal. In one embodiment, the reflectance is examined through a linear polarizer (henceforth referred to as the analyzer) in two configurations. In the first of these configurations, the analyzer is oriented parallel to the illumination polarization, passing the surface signal ($I_{surface}$), and half of the depolarized bulk signal ($I_{bulk}$). Next, the analyzer is oriented perpendicular to the illumination polarization, blocking the majority of the surface signal, while again passing half of the bulk signal.

Thus, the total intensity of the parallel-polarized reflectance, Ipar, is the sum of the surface signal and half of the bulk signal, whereas the perpendicular polarized signal is composed only of half the bulk signal. With this, it is possible to separately image the sample in both parallel and perpendicular analyzer configurations. The perpendicular image Iper may then be arithmetically subtracted from the parallel image to produce a difference image limited to signal received from the surface reflectance:

$$I par = I surface + \tfrac{1}{2} I bulk$$

$$I per = \tfrac{1}{2} I bulk$$

$$I par - I per = I surface$$

Figure 1A:
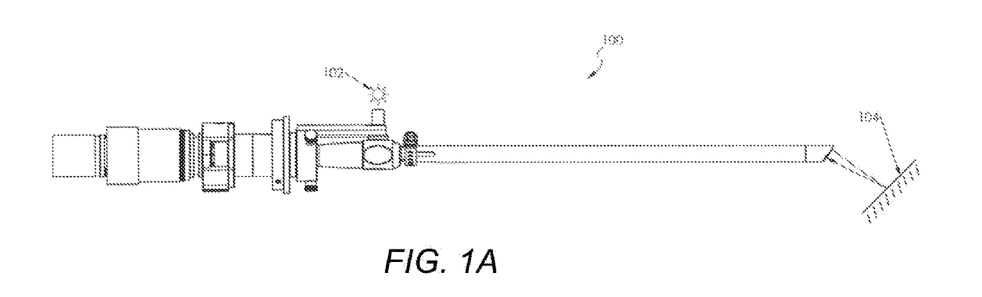
FIG. 1A is a schematic illustration of a laparoscopic implementation of a differentially polarized light imaging system according to the invention, FIG. 1B provides an exploded view of the instrument of FIG. 1A.

FIG. 1A shows a modified laparoscopic system 100 according to the invention. An illuminating light source 102 delivers light to the instrument 100. The illuminating light is polarized and directed to a target tissue region 104. The reflected/scattered light is collected by the instrument for image acquisition and analysis. The terms "laparoscope" and "laparoscopic" as used herein are intended to generally encompass instruments, such as conventional laparoscopes as well as thoracoscopes, arthroscopes, bronchoscopes, colonoscopes, cystoscopes, endoscopes, entereroscopes, hysteroscopes, laryngoscope, mediastinoscopes, sigmoidoscopes, pleuroscopes, esophagoscopes, and ureteroscopes, that can perform diagnostic, minimally invasive diagnostic or therapeutic tasks by insertion either into a body orifice or by small incisions to access internal tissue.

Figure 1B:
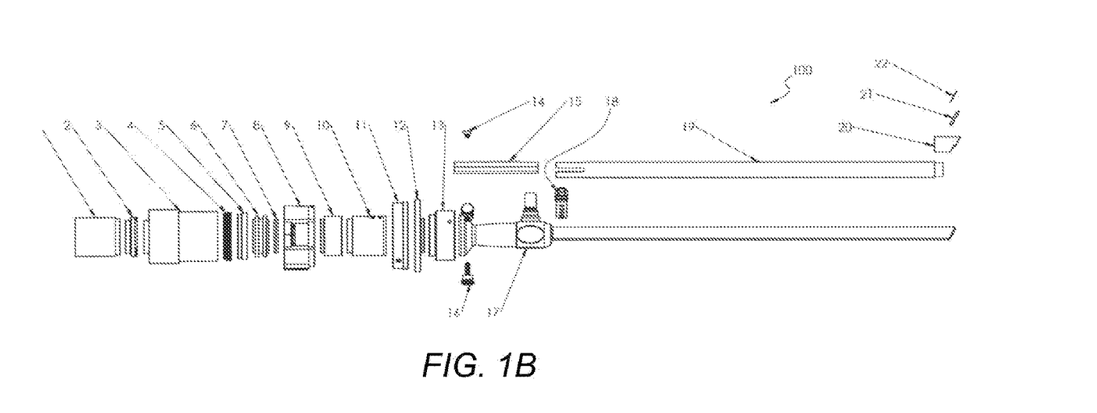

FIG. 1B provides an exploded view of the system 100 of FIG. 1A, including most notably a detector camera 1, a lens 3, a linear analyzer 7, a liquid crystal variable wavelength retarder 10, a laparoscope 17, and a distal polarizer 22. (Other elements shown in the exploded view include various threading adaptors 2, 4, 5, 11 and 12; rotating optical mount 8; lens tube 9; lens rod coupler 13; radial clamp 18 and laparoscope sheath 19.)

Figure 2A:
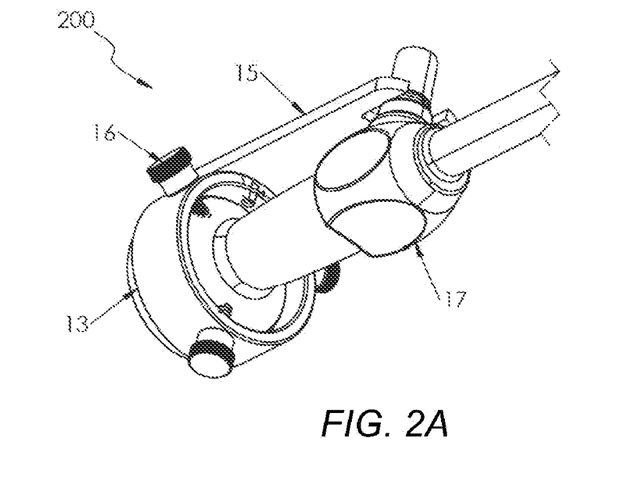
FIG. 2A illustrates a mechanism for joining the proximal optics to the laparoscopic lens rod, FIG. 2B provides an exploded view of the joinder mechanism of FIG. 2A.
Figure 2B:
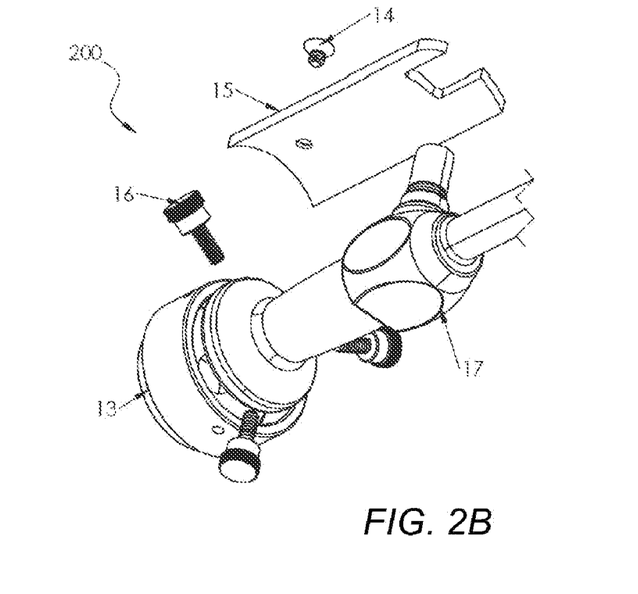

FIG. 2A shows a mechanism 200 for mating the laparoscope to the proximal optics of the system. FIG. 2B provides an exploded view of this mechanism. Here a series of three radial set screws 16 serve to secure the proximal end of the laparoscope to a coupler 13 attached to the proximal optical train 1-12 (See FIG. 1B). Constraining plate 15 enforces the proper radial orientation of the laparoscope 17 with respect to the proximal optical train.

Figure 3A:
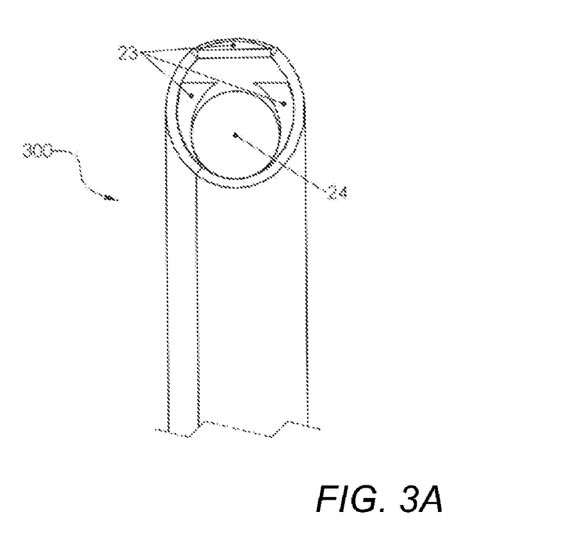
FIG. 3A is an illustration of a polarizing end cap adapted for use with a conventional laparoscope according to the invention, FIG. 3B provides an exploded view of the end cap of FIG. 3A.
Figure 3B:
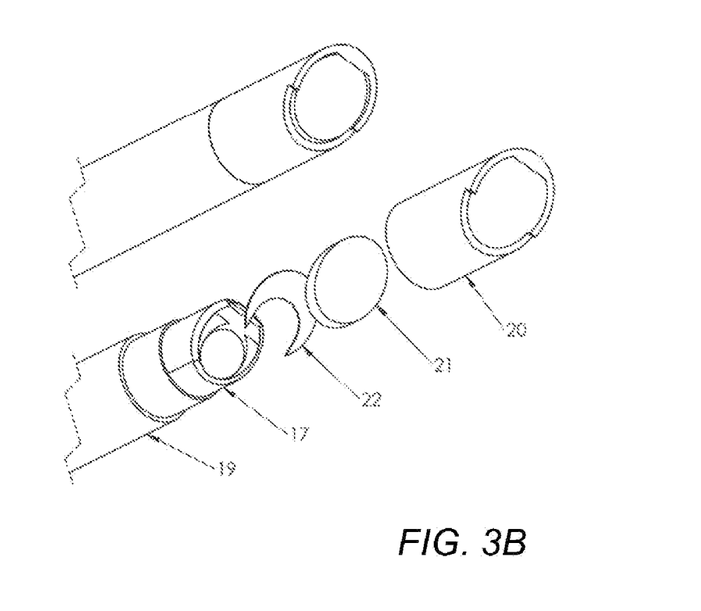

FIG. 3A illustrates a distal assembly 300 which can serve to linearly polarize the illumination output of the laparoscope. With reference as well to exploded view of FIG. 3B, polarizing film 22 is secured over the illumination outputs 23 via a stainless steel housing 20 covered at one end by a glass plate 21. The crescent shape of the polarizing film 22 allows coverage of the illumination outputs 23 of the laparoscope, while leaving clear the aperture 24 for collection of the sample reflectance. The distal end cap housing 20 can be joined to laparoscope sheath 19 by various connection mechanisms, e.g., a threaded connection, a frictional fitting, a snap seal connection or adhesives.

With reference again to FIG. 1, the laparoscope optic 17 itself can consist of a ~30 cm long metal tube containing a conventional fiber optic and a gradient index (GRIN) lens (not shown). The fiber optic delivers polarized light to the target site undergoing examination, while the GRIN lens receives the reflectance image returned from the sample and relays it to the proximal (left) end of the laparoscope 17. At this point, the signal passes a wavelength retarder 10 and a linear analyzer 7. Depending on the state of the retarder, either the parallel or perpendicular component of the image is passed by this pair of optics. The use of an electrically controlled variable wavelength retarder in this case enables rapid switching between the components for video-rate acquisition. The resulting signal is then focused by a zoom lens 3 onto a sensor, e.g., a color CCD camera, 1 for imaging.

The sensor 1 can be a RGB camera. The CCD arrays used by these types of cameras are covered by a great number of red, green, and blue color filters in an arrangement referred to as Bayer tiling. The signal read from this array forms the raw Bayer-tiled image, which is then read by a color processing algorithm to produce the final image. Depending on the algorithm applied, the resulting image may be in RGB color or in monochrome. In the former case, for every pixel in the array, a red, green, and blue intensity value is extrapolated from neighboring color pixels and the pixel itself, creating an image with the same spatial resolution as the raw Bayer tile array, but where each pixel has a red, green, and blue value associated with it instead of just its filter's color. In the monochrome case, a single intensity value is calculated for each pixel as the weighted average of the three-color intensities in the local area.

In either case, the intensity values for each pixel can be recorded by the camera. This camera's CCD has a greater intensity resolution than the 8-bit resolution typically applied in laparoscopes. This substitution concerning sensitivity was made because the DPL signal is at least an order of magnitude weaker than the total reflectance. Thus, to effectively resolve this signal in detail a greater intensity resolution is required than that typically applied in regular endoscopic reflectance imaging. Following the collection of the parallel and perpendicular polarized images, each of the corresponding intensity values in the perpendicular image is subtracted from its corresponding value in the parallel image in software. This is straightforward for monochrome images, where corresponding subtracted pixels share the same position, and only slightly more complicated for RGB images. For RGB images, the raw Bayer-tiled image is recorded without any of the camera's color-processing algorithms applied to avoid any potential artifacts that may be introduced when applied prior to subtraction (this mostly concerns automatically applied color correction). The images are then subtracted from one another in the same manner as in the monochrome case, after which an RGB color image is generated from the Bayer-tiled difference image via a simple linear color processing algorithm without correction.

While not necessarily a vital feature of DPL imaging, the ability of the system to image in RGB is not simply a novelty, it does provide additional practical information beyond what is gleaned in monochrome. At the very least, it allows the system to meet the original capabilities of conventional non-polarizing laparoscopes, which image in RGB color. However, in addition to this, the low resolution spectral information provided by the three color channels can prove useful when trying to resolve lesions more clearly.

To calibrate the system prior to use, a mirror image of the illumination is resolved. To ensure the analyzer 7 transmission axis and the illumination polarization are oriented appropriately relative to each other, a mirror image of the illumination is resolved by the system, and the analyzer 7 is rotated while monitoring the live intensity average. Once this intensity is minimized, the analyzer orientation is noted as perpendicular to the illumination. The parallel orientation is then denoted as the perpendicular orientation plus 90 degrees. After fixing the analyzer in the parallel orientation, the variable wavelength retarder is placed in position and set to approximately half-wavelength retardance. When the illumination source is white light or contains multiple wavelengths or wavelength bands, it can be advantageous to set the half-wavelength retardance to a "best-fit" value. For example, when white light (or visible light) illumination is used, optimizing the system for green light differential images can be advantageous even though some attenuation will occur in the red or blue differential images. The slow axis of the retarder 10 is then rotated relative to the analyzer 7. Like the calibration of the analyzer, once the angular position of the retarder is found where the average image intensity is at an extremum (minimized in this case), the retarder's slow axis should be oriented 45 degrees offset from the analyzer. At this point, the retarder is fixed at this position.

Next, the optimal zero and half-wavelength retarding voltages of the retarder are determined. Retardance may be driven to near zero simply with the application of a high voltage, with subtle retardance variation with wavelength. This easily establishes the zero retardance voltage at the maximum operating voltage, 25V. Conversely, the voltage required to enforce half-wave retardance varies more with wavelength, ranging from 1.3 to 1.7V over the range of camera-visible wavelengths (~405-635 nm).

For example, the optimal half-wavelength retardance voltage is calibrated as follows: with the retarder's slow axis oriented 45 degrees from the analyzer axis and the analyzer axis oriented parallel to the illumination polarization (both achieved earlier), the voltage of the retarder is varied while imaging the incoming polarized light from the mirror image of the illumination. As the voltage is varied, the signal received by the camera will approach a minimum as the mirrored polarized illumination is rotated out of alignment with the analyzer transmission axis.

Because the half-retardance voltage is dependent on wavelength, there will be a different voltage for the signal minimum in each color channel. However, there will be a single voltage associated with the minimum for the intensity averaged across all color channels, this voltage can be used as an approximation in place of custom voltages for each color channel. To estimate the value of this singular voltage, the signal minimum from the green channel was used (~1.4V), on the basis that the half wave voltage for the green channel should lie between that of the red and blue, while also catering to the camera's increased sensitivity to green. With this, the two operating voltages of the retarder are now established: 25V for zero retardance, and 1.4V for half-wavelength retardance.

Once these optical elements are calibrated appropriately, the system is ready to start capturing images. As the camera finishes exposing each frame, it signals the retarder voltage controller to switch between its operating voltages, syncing the switch with the data reading period following the exposure of each frame.

Figure 4:
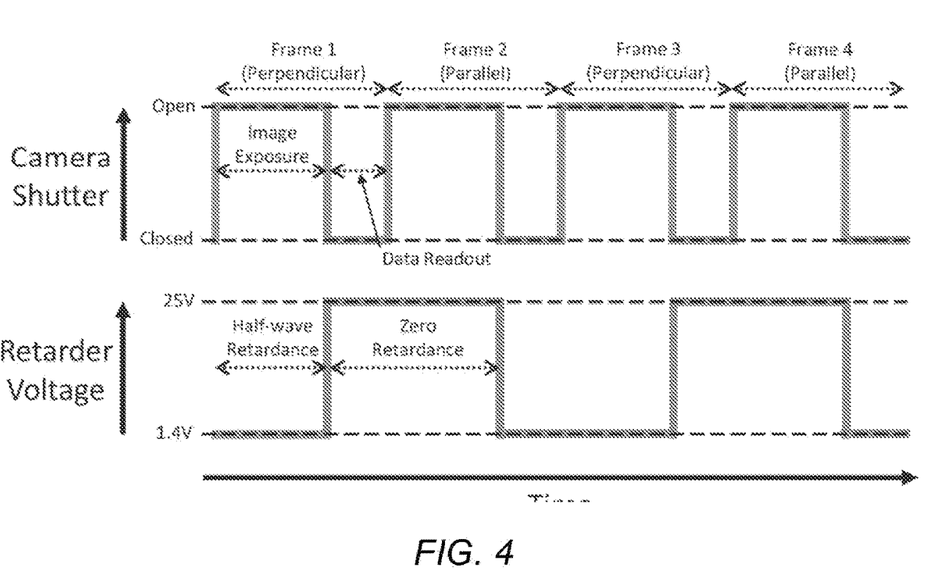
FIG. 4 is a diagram illustration of an acquisition protocol for DPL imaging according to the invention.

FIG. 4 illustrates one embodiment of a data acquisition protocol. This protocol results in the recording of a series of images whereby the first image is captured during the collection of the parallel polarized reflectance, the second during the perpendicular, and so forth alternating in this way at the camera's frame rate. For every pair of polarized images, the difference and sum of the pair are computed, displayed, and written to disk on a connected computer. Several imaging parameters may be changed during live imaging, including the weighting of parallel and perpendicular images, along with the amplification of the resulting images. Following the completion of image collection, the raw imaging data is saved and a copy is converted to video for later viewing.

The designs disclosed herein are only a few of the possible configurations capable of DPL imaging. Alternatives include the use of two cameras and a combination of optical elements that separates the parallel and perpendicular components of the reflectance and directs each to its own camera. The advantage to having such a two-camera system relative to a singular one is that given all the cameras used here have the same max frame rate, a two-camera system would be able to stream DPL images at this max frame rate, while a single camera system would only be able to do so at half this frame rate. This follows from the single camera having to image two frames (parallel and perpendicular) for every DPL frame produced, while in the two-camera setup each of these two component frames is collected by a separate camera, allowing the resulting DPL image stream to be collected at the full framerate.

In another embodiment, a polarizing camera can be used as the analyzing optic. For example, polarizing CCD cameras are currently available that can record simultaneous images in different polarization states. One such polarizing camera is the Blackfly S USB3 camera available from FLIR, Inc. (Arlington, Va.). A polarizing CCD camera typically is comprised of four different angled polarizers (90°, 45°, 135° and 0°), which are placed on each pixel. The relationship between two or more of the images captured via the different polarizers permits a calculation of DPL at full frame rate.

In yet another alternative, one can use different polarization states of the scattered light from which the DPL image may be calculated. In the prior embodiment, the parallel and perpendicular images are acquired to calculate the DPL image. However, the DPL image may also be calculated from the unpolarized image and the parallel image, the unpolarized image and the perpendicular image, and other image pairs that together contain both parallel and perpendicular polarization information, while at least one contains information exclusive to parallel or perpendicular on its own.

Additionally, while this particular embodiment exploits the linear parallel and perpendicular polarization of light, in other applications circular R and L polarized light may be substituted to similar effect, but with a lesser degree of bulk signal removal.

EXAMPLES

The following data was obtained during feasibility trials conducted at Lahey Clinic. The data present a direct comparison between conventional imaging (unpolarized) and differential polarized light (DPL) imaging.

Fields were selected containing features suspected to be cancerous lesions. For each of these fields, a region of interest (ROI) was drawn circumscribing the suspected lesion. In order to quantify the difference in the visibility of this lesion between unpolarized and DPL imaging, the contrast of the defined lesion (clear area within gray area) with the surrounding tissue (defined by the gray area) was computed. This was achieved by calculating the mean pixel intensity within the lesion and surrounding tissue areas and the Weber contrast between these mean values. (Weber contrast is calculated as the difference in the mean intensities of the lesion and the surrounding tissue divided by the mean intensity of the surrounding tissue.) The results were plotted for each color channel collected by the camera for both unpolarized and DPL images.

Figure 5:
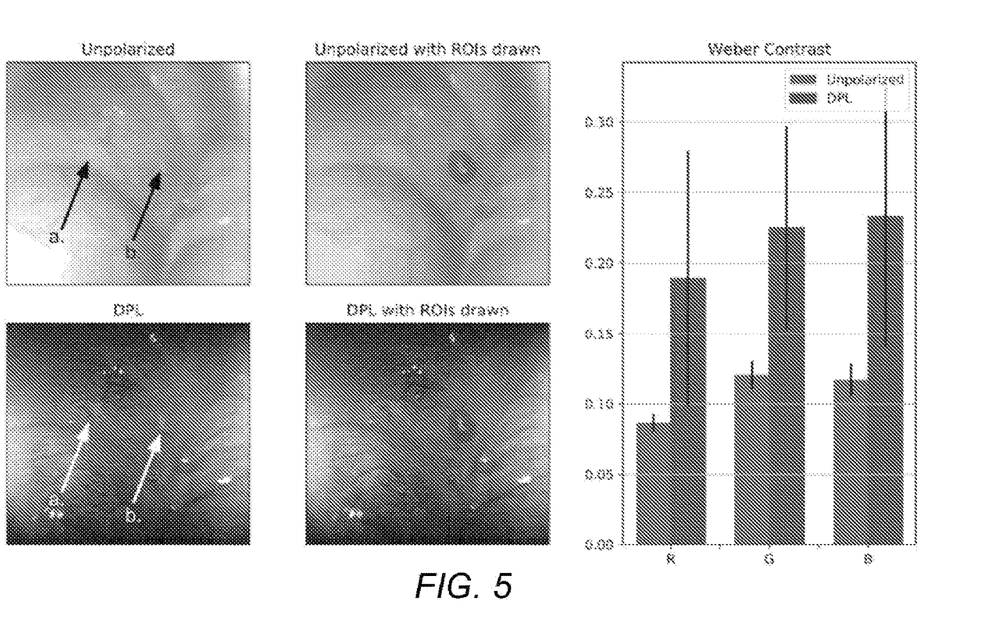
FIG. 5 presents a series of photographs comparing unpolarized images and images obtained by DPL imaging according to the invention.

FIG. 5 shows that visibility is significantly improved in all color channels for a small lesion on a bowel segment (labelled "b"). Further textural features (labelled "a") can also be seen in the DPL image that are not present in the unpolarized image.

Figure 6:
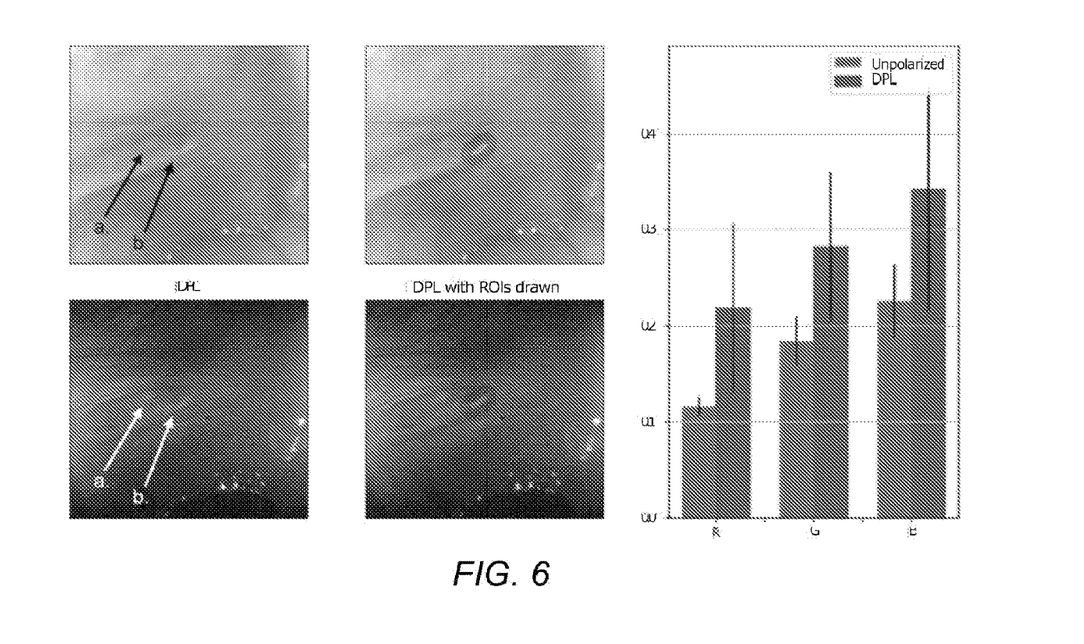
FIG. 6 presents another series of photographs comparing unpolarized images and images obtained by DPL imaging.

FIG. 6 provides a second example of improved visualization of a suspected lesion (again, labelled "b"), as well as a possible occult lesion (labelled "a").

Figure 7:
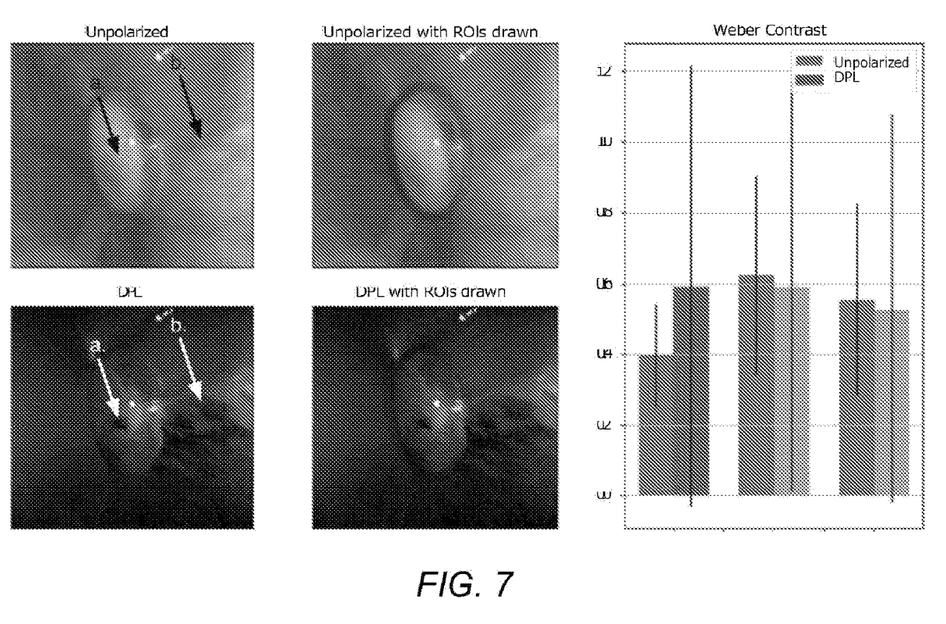
FIG. 7 presents yet another series of photographs comparing unpolarized images and images obtained by DPL imaging.

FIG. 7 shows a third example of improved visualization of a cancerous lesion as well as possible infiltration on the right lower quadrant of peritoneum. In this case, the visibility of the feature is not significantly improved. However, there are several new textural features (a, b) which appear in the DPL of this field that were not evident before.

Figure 8A:
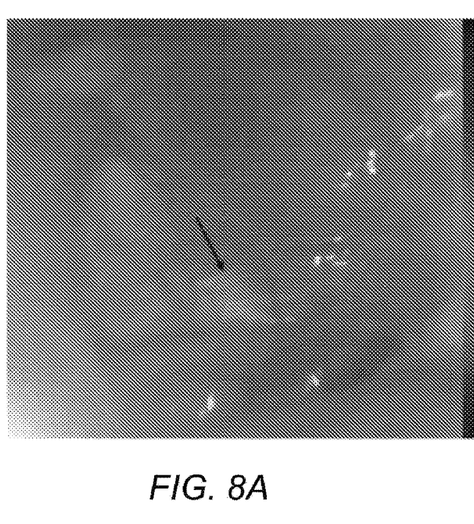
FIG. 8A is an unpolarized image of a tissue region.
Figure 8B:
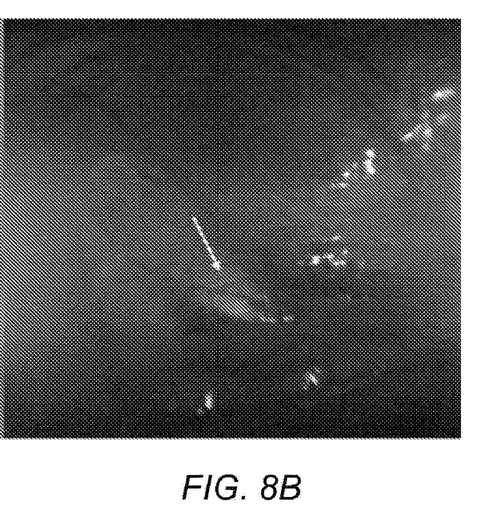
FIG. 8B is a DPL image of the same region.

FIG. 8A is an unpolarized image and FIG. 8B is the DPL image of another tissue region. These images are not necessarily related to lesion visualization, but demonstrate other potentially useful information obtainable with the present invention. It is suspected that the mechanism behind the disparity in the unpolarized image (FIG. 8A) and DPL image (FIG. 8B) of certain tissue features is related to collagen structure. While collagen fibers in tissue can vary in density, orientation, size, and cross-linking, unpolarized imaging is primarily sensitive to only density and size, with higher fiber densities and sizes scattering more and producing a whiter feature. On the other hand, changes in the other properties of the fibers have less impact on the signal from a sample of a given fiber size and density. Although the DPL signal is related to fiber size and density as well, it is also likely sensitive to fiber orientation/organization due to its polarized nature. In this way, two patches of collagen may look like two indistinguishable white features in an unpolarized image, but if they differ in organization, they may look markedly different in polarized imaging. Here a relatively large uniform white feature is evident in the unpolarized image. DPL attenuates the majority of the area of this feature with the exception of the lower right portion marked by the arrow. This may imply differences in collagen structure, or that the lower right portion is more superficial than the rest.

It has been shown in the past that there are pathologies that can affect the organization of collagen. These pathologies can include cancerous/metastatic tissue development, with significant differences in collagen organization arising between healthy and diseased tissue. Beyond this, in the early stages of cancer tissue growth, the collagen density is not changed very much; rather, the cross-linkage and organization is first to be modified. Thus, DPL imaging may provide early detection of physiological/histological changes (e.g., cancer, fibrosis or wound healing) not yet visible with unpolarized imaging.

Figure 9A:
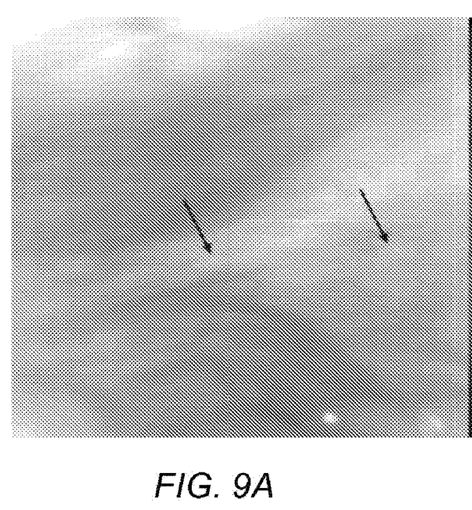
FIG. 9A is an unpolarized image of another tissue region.
Figure 9B:
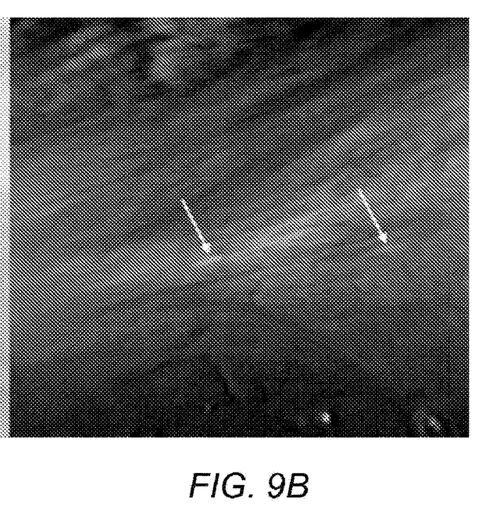
FIG. 9B is a DPL image of the same region.

FIGS. 9A and 9B provide another example of improved tissue characterization with DPL imaging. FIG. 9A is an unpolarized image and FIG. 9B is the DPL image of the same region. In this field, two occult spots marked by arrows become evident in DPL.

Figure 10A:
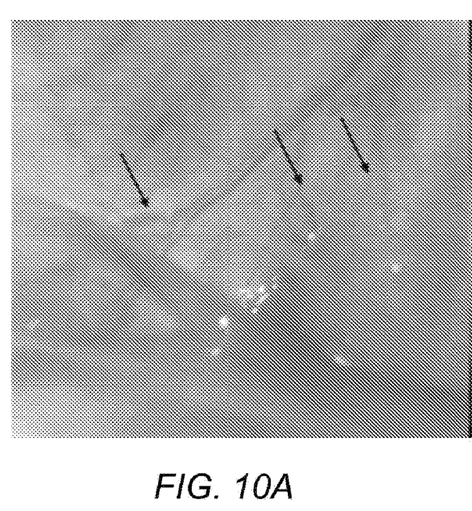
FIG. 10A is an unpolarized image of yet another tissue region.
Figure 10B:
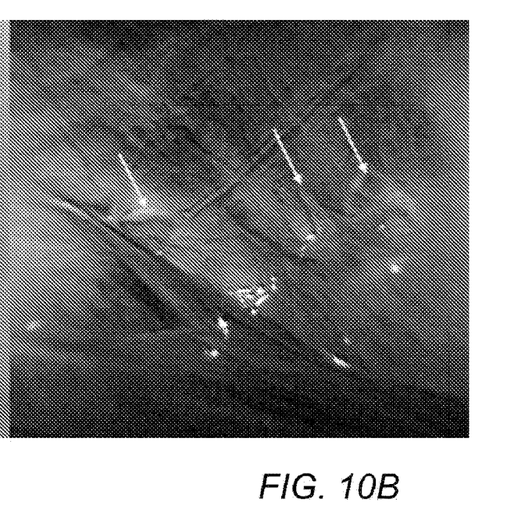
FIG. 10B is a DPL image of the same region.

FIGS. 10A and 10B provide a further example of improved tissue characterization with DPL imaging. FIG. 10A is an unpolarized image and FIG. 10B is the DPL image of the same region. Several white spots and filaments become much more clearly visualized in DPL image.

Figure 11A:
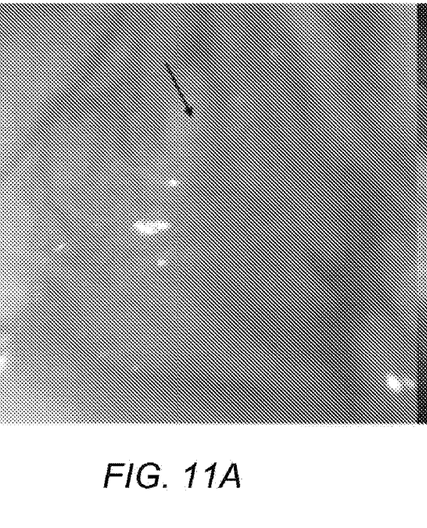
FIG. 11A is an unpolarized image of yet another tissue region.
Figure 11B:
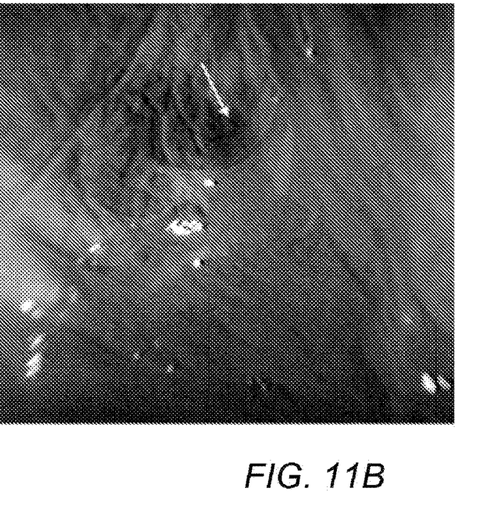
FIG. 11B is a DPL image of the same region.

FIGS. 11A and 11B provide yet another example of improved tissue characterization with DPL imaging. FIG. 11A is an unpolarized image and FIG. 11B is the DPL image of the same region. Interestingly, in this case, there is a new phenomenon. Firstly, as in the prior images, there are white spots and filaments whose visibility is enhanced in DPL. However, now there is also a white spot in unpolarized (arrow) which darkens in DPL instead, suggesting a difference in the collagen organization in this region compared to the white spots in prior images.

Figure 12A:
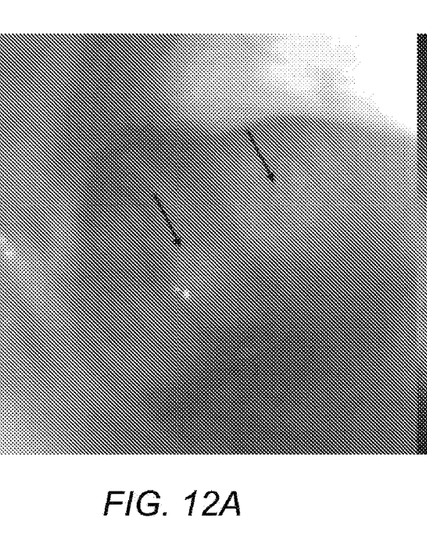
FIG. 12A is an unpolarized image of yet another tissue region.
Figure 12B:
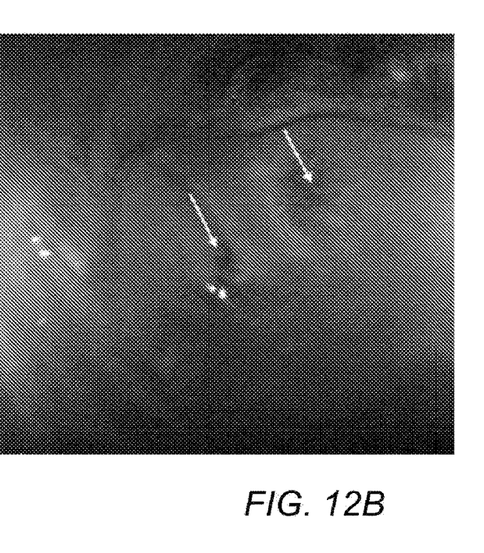
FIG. 12B is a DPL image of the same region.

FIGS. 12A and 12B provide a further example of improved tissue characterization with DPL imaging. Again, FIG. 12A is an unpolarized image and FIG. 12B is the DPL image of the same region. The figures provide a second example of this darkening phenomenon.

Figure 13A:
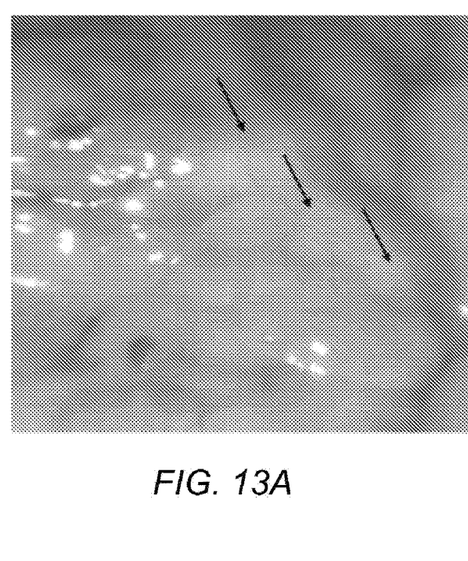
FIG. 13A is an unpolarized image of yet another tissue region.
Figure 13B:
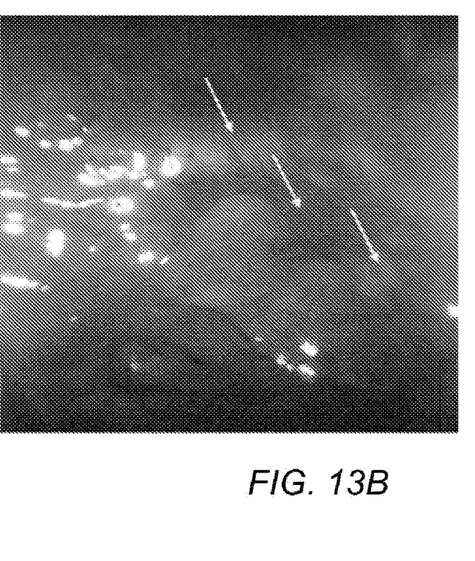
FIG. 13B is a DPL image of the same region.

Finally, FIGS. 13A and 13B provide a further example of improved tissue characterization with DPL imaging. Again, FIG. 13A is an unpolarized image and FIG. 13B is the DPL image of the same region. These figures show a ribbon of muscle that demonstrates preferential orientation of fibers in the direction parallel to the muscle. Tracking this ribbon from top to bottom, the direction the tissue is oriented relative to the viewer perspective shifts from more vertical (top arrow), to more horizontal (middle arrow), to more horizontal again (bottom arrow). While the intensity of the unpolarized signal along this track for the muscle remains uniform, the DPL intensity appears to vary with the relative muscle orientation, going from light to dark to light again.

Thus, these figures collectively demonstrate features that look similar in unpolarized (e.g., white spots in FIGS. 9-12 but are distinct in DPL (spots in FIGS. 9-10 compared to those in FIGS. 11-12). This indicates sensitivity to a tissue property that is not available in unpolarized imaging. Again, it is hypothesized that this property is collagen organization/orientation. The variance in this organization may be due to healthy tissue heterogeneity (e.g., wound healing), or pathologies (e.g., cancer fibrosis or inflammation).

To demonstrate a scenario in which the DPL modality improves contrast in a controlled lab setting, an optical phantom was fabricated from PDMS (polydimethylsiloxane, similar to clear silicone rubber) where two different preparations of PDMS were used. The first mixture was prepared from 0.9519% g/g zinc oxide (ZnO), a white powder which was mixed with the PDMS to be used as the material from which the square features were made. The second mixture was prepared from 0.0419% g/g titanium dioxide (TiO 2), another white powder which was mixed with the PDMS to be used as the material from which the background was made.

The resulting phantom consists of a titanium dioxide/PDMS background with an array of zinc oxide/PDMS features embedded at the surface which decrease in thickness from left to right, and decrease in cross-section from top to bottom.

Figure 14:
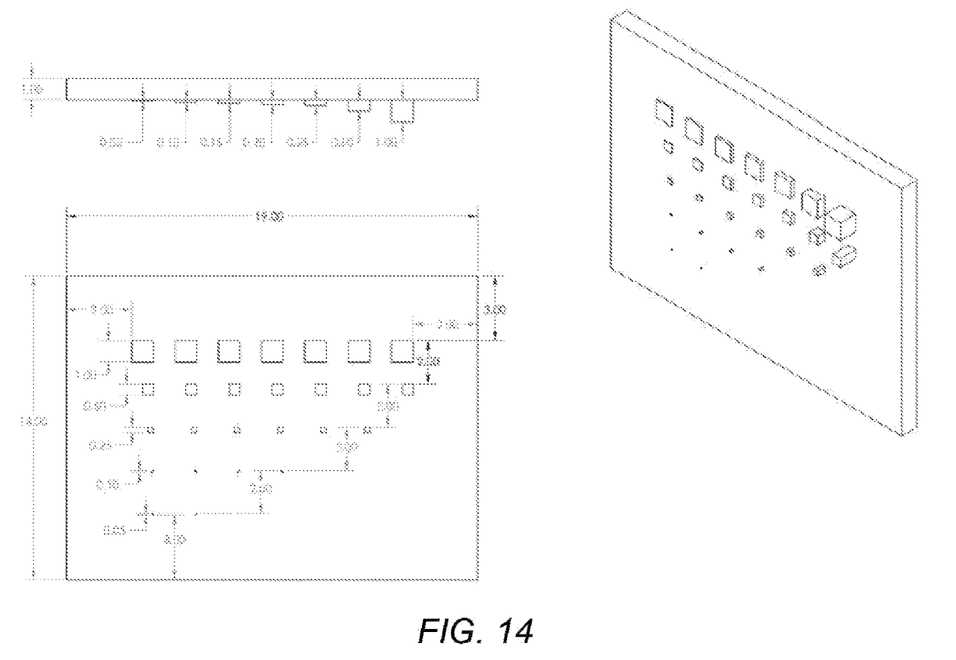
FIG. 14 is a schematic illustration of the geometry of a mold that was used to generate the background PDMS with holes of varying depths and sizes.

FIG. 14 shows the geometry of the mold that was used to generate the background PDMS with holes of varying depths and sizes. These holes were later filled with the feature PDMS mixture.

Figure 15:
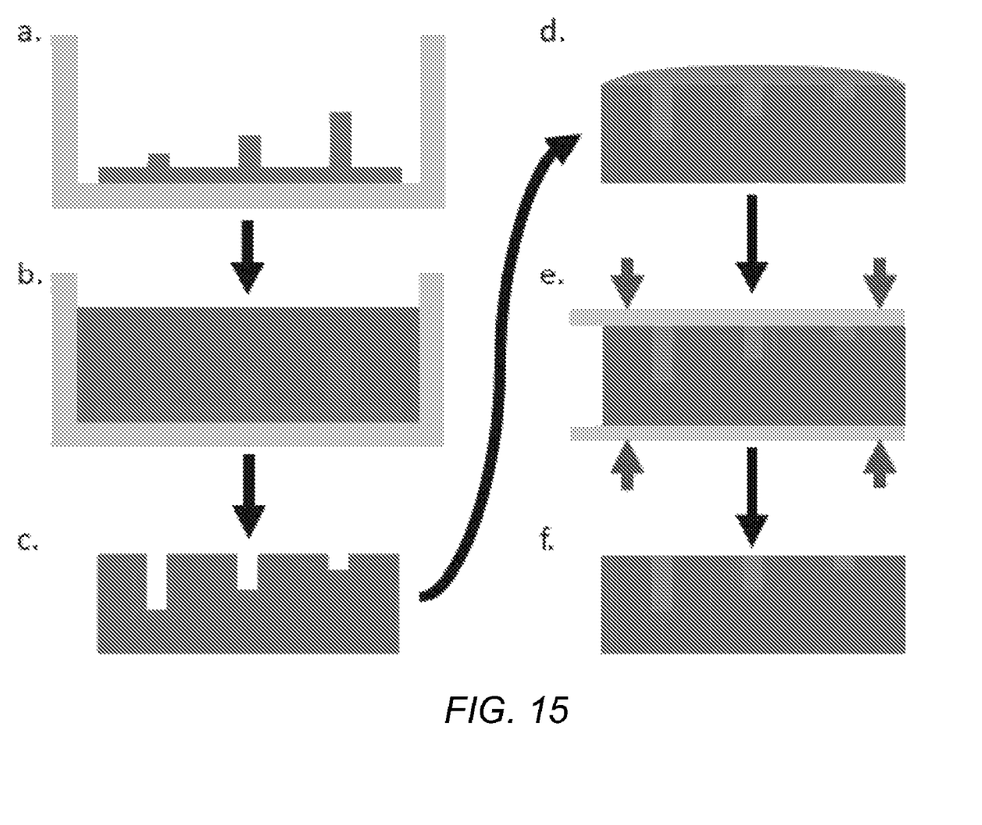
FIG. 15 is a block diagram of fabrication process for the mold of FIGS. 14.

FIG. 15 is a block diagram of the mold fabrication process.

Figure 16:
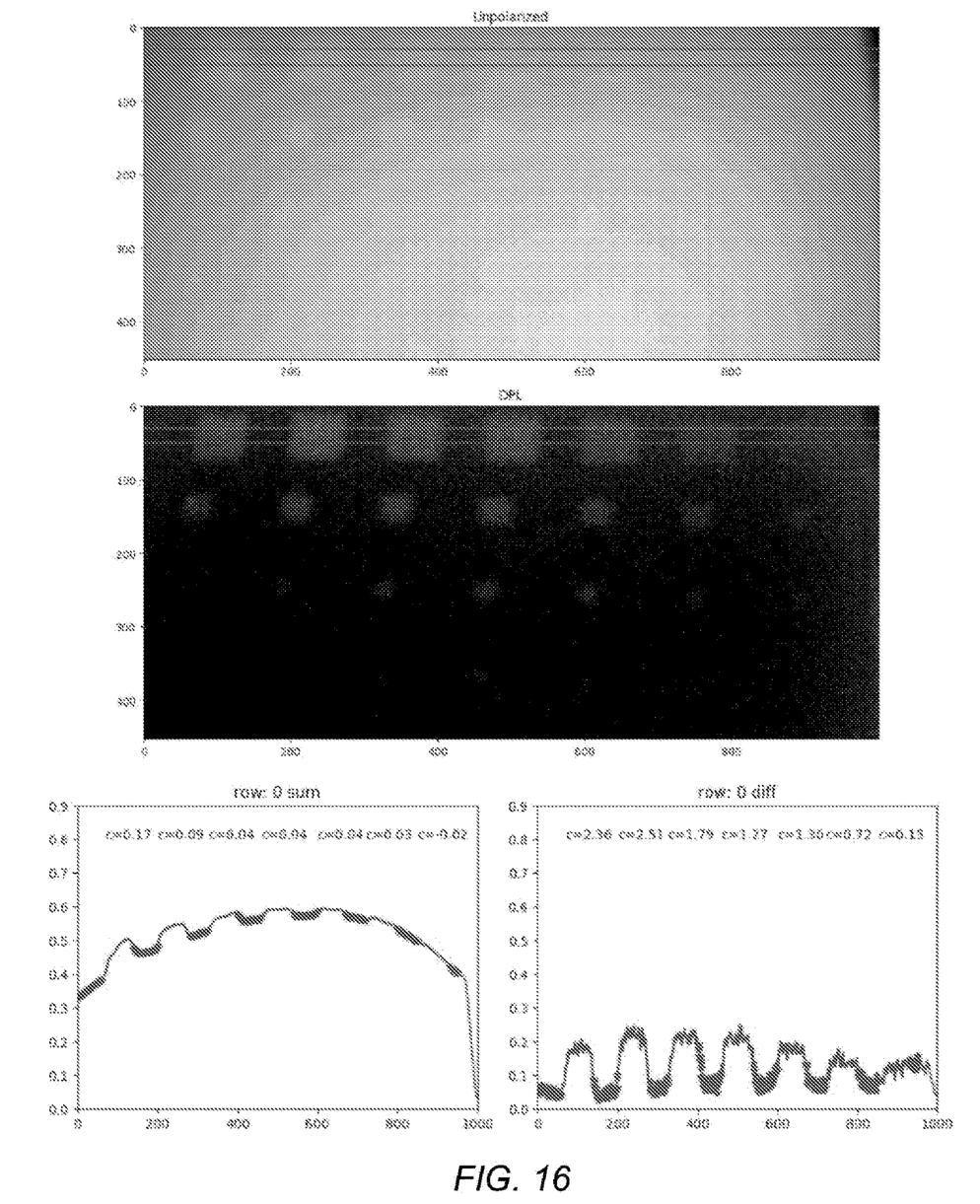
FIG. 16 provided unpolarized and DPL views of the test mold of FIG. 14.

FIG. 16 provided unpolarized and DPL views of the test mold. It can be seen from these views that the PDMS mixtures demonstrated poor visibility/contrast in unpolarized imaging (SUM), while they are much more clearly visualized in DPL.

To take a more quantitative look at the contrast of the features against the background, the intensity along the top row of features was taken along two rows, as further shown in FIG. 16. It appears that the increased contrast in the DPL mode is due to the difference in particle size or morphology of the powders, which would affect the scattering distribution of the particle and resulting polarization of the backscattered light. This effect on the polarization would only be evident in the DPL mode, granting it a source of contrast not available to the unpolarized mode. Thus, when the concentrations of the two white powders are tuned such that they are nearly the same intensity in unpolarized imaging, a difference can still be seen in DPL. In this case, it is hypothesized that while the intensity of the light coming off the features and background is of a similar magnitude, the polarization quality between the two is different, resulting in a difference in visualization in DPL.

While the present invention is described in connection with what is presently considered to be the most practical and preferred embodiments, it should be appreciated that the invention is not limited to the disclosed embodiments, and is intended to cover various modifications and equivalent arrangements included within the spirit and scope of the claims. Modifications and variations in the present invention may be made without departing from various aspects of the invention as defined in the claims. Accordingly, the invention is not to be limited by what has been particularly shown and described.

All publications and references cited in the present application are herein expressly incorporated by reference in their entirety.

The invention claimed is:

1. A laparoscopic, thoracoscopic, or endoscopic imaging system for internal tissue characterization comprising:
   an optical input port for receiving illuminating radiation,
   at least one optical illumination waveguide for directing illuminating radiation along an optical illumination path from the input port to a target tissue region to be examined,
   at least one polarizing optic disposed in the optical illumination path configured to polarize the illuminating radiation directed to the tissue region,
   an optical collection waveguide having a distal end aperture for collecting backscattered radiation from the tissue region and further having a proximal end for transmitting the backscattered radiation to a detector, the detector and optical collection waveguide defining an optical return path,
   at least one lens disposed in the optical return path for imaging the tissue region unto the detector, and at least one analyzing optic also disposed in the optical return path, whereby backscattered radiation of differing polarizations can be passed to the detector to generate first image data corresponding to a retained first linear polarization of the illuminated radiation and second image data corresponding to a second linear polarization of the backscattered radiation different than the first linear polarization or corresponding to unpolarized backscattered radiation.

2. The system of claim 1 wherein the optics of the return path further comprises a variable wavelength retarder.

3. The system of claim 1 wherein the analyzing optic comprises a polarizing camera.

4. The system of claim 1 wherein the optics of the return path further comprises an adjustable focus lens.

5. The system of claim 1 wherein the system further comprises a constraining plate for joining the collection waveguide directly or indirectly to the analyzing optic in a manner which maintains a desired radial orientation between the illumination and return path optics.

6. An optical adapter for a laparoscope, thoracoscope, or endoscope to permit differential polarization imaging of internal tissue, the adapter comprising:
　an end cap housing having a generally cylindrical shape and a fitting for mating with a distal end of a laparoscope,
　at least one polarizing window optical aligned with an illumination source to transmit polarized radiation to a target tissue region to be examined, and an aperture for collecting backscattered radiation of differing polarizations following illumination of the tissue region, the aperture in optical communication with a collection waveguide of the laparoscope,
　wherein the backscattered radiation has a retained first linear polarization of the polarized radiation and either a second linear polarization different than the first linear polarization or is unpolarized backscattered radiation.

7. The adapter of claim 6 wherein the end cap housing is joined to the laparoscope by a threaded connection, a frictional fitting, a snap seal connection or adhesives.

8. The adapter of claim 6 wherein the fitting is a threaded connection.

9. The adapter of claim 6 wherein the fitting is a snap seal fitting wherein one or more protuberances on one of the inside of the end cap body or the outside of the laparoscope mates with a corresponding recess on the other of the inside of the end cap body or the outside of the laparoscope and, optionally, wherein the protuberance comprises an annular ring and the recess comprises an annular groove wherein the ring is located on either the inside of the end cap body or the outside of the laparoscope and mates with a corresponding recess on the other of the inside of the end cap body or the outside of the laparoscope to provide a snap-seal fitting.

10. A method of laparoscopic, thoracoscopic, or endoscopic examination of a target tissue region, comprising:
　illuminating a target tissue region with radiation having a first defined illumination polarization,
　acquiring a first image of the tissue region by detecting scattered radiation that retains said first illuminating polarization,
　acquiring a second image of the tissue region from scattered radiation having a polarization different from said illuminating polarization, and
　deriving a differential polarization image from said first and second images,
　wherein the first image is obtained by detecting scattered radiation that retains a first linear polarization of the illuminating radiation and the second image is obtained by detecting scattered radiation that is unpolarized.

11. The method of claim 10 wherein the target tissue region is illuminated with polarized light comprising a range of wavelengths.

12. The method of claim 11 wherein the first and second images are acquired at two or more wavelengths or as color images.

13. The method of claim 12 wherein the first and second images are acquired serially with one or more cameras.

14. The method of claim 12 wherein the first and second images are acquired at the same time with one or more cameras.

15. The method of claim 10 wherein the first and second images are obtained with a polarizing camera.

16. The system of claim 2 wherein voltages applied to the variable wavelength retarder are set to enhance differential imaging across a spectrum of visible wavelengths.

17. A method of laparoscopic, thoracoscopic, or endoscopic examination of a target tissue region, comprising:
　illuminating a target tissue region with radiation having a first defined illumination polarization,
　acquiring a first image of the tissue region by detecting scattered radiation that retains said first illuminating polarization,
　acquiring a second image of the tissue region from scattered radiation having a polarization different from said illuminating polarization, and
　deriving a differential polarization image from said first and second images,
　wherein the first image is obtained by detecting scattered radiation that retains a first linear polarization of the illuminating radiation and the second image is obtained by detecting scattered radiation that is unpolarized or has a linear polarization different from the illuminating radiation.

18. A method of laparoscopic, thoracoscopic, or endoscopic examination of a target tissue region, comprising:
　illuminating a target tissue region with radiation having a first defined illumination polarization,
　acquiring a first image of the tissue region by detecting scattered radiation that retains said first illuminating polarization,
　acquiring a second image of the tissue region from scattered radiation having a polarization different from said illuminating polarization, and
　deriving a differential polarization image from said first and second images,
　wherein the first image is obtained by detecting scattered radiation that retains a first circular polarization of the illuminating radiation and second image is obtained by detecting scattered radiation that is either unpolarized or has a circular polarization different from the illuminating radiation.

* * * * *